US008871742B2

(12) United States Patent
Marcum et al.

(10) Patent No.: US 8,871,742 B2
(45) Date of Patent: *Oct. 28, 2014

(54) COMPOSITION AND METHOD FOR TREATING CONNECTIVE TISSUE DAMAGE

(71) Applicant: ArthroDynamic Technologies, Animal Health Division, Inc., Lexington, KY (US)

(72) Inventors: Frank D. Marcum, Lexington, KY (US); John William Seanor, Lexington, KY (US); Foster Harold Northrop, Crestwood, KY (US)

(73) Assignee: ArthroDynamic Technologies, Animal Health Division, Inc., Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/891,979

(22) Filed: May 10, 2013

(65) Prior Publication Data
US 2013/0251781 A1    Sep. 26, 2013

Related U.S. Application Data

(63) Continuation of application No. 11/766,510, filed on Jun. 21, 2007, now Pat. No. 8,455,458, which is a continuation-in-part of application No. 11/015,137, filed on Dec. 17, 2004, now Pat. No. 7,485,629, and a continuation-in-part of application No. 11/105,163, filed on Apr. 13, 2005, now Pat. No. 7,504,387.

(51) Int. Cl.
| A61K 31/737 | (2006.01) |
| A61K 31/726 | (2006.01) |
| A61K 31/7008 | (2006.01) |
| A61K 31/715 | (2006.01) |
| A61K 35/12 | (2006.01) |
| A61K 45/06 | (2006.01) |
| A61L 27/26 | (2006.01) |
| A61K 38/18 | (2006.01) |
| A61K 31/728 | (2006.01) |
| A61K 31/56 | (2006.01) |
| A61L 15/22 | (2006.01) |
| A61L 17/10 | (2006.01) |
| A61B 17/064 | (2006.01) |
| A61B 17/06 | (2006.01) |
| A61B 17/00 | (2006.01) |

(52) U.S. Cl.
CPC ............. *A61K 31/737* (2013.01); *A61K 31/715* (2013.01); *A61K 35/12* (2013.01); *A61B 17/064* (2013.01); *A61K 45/06* (2013.01); *A61L 27/26* (2013.01); *A61K 38/18* (2013.01); *A61B 17/06166* (2013.01); *A61B 2017/00004* (2013.01); *A61K 31/728* (2013.01); *A61K 31/56* (2013.01); *A61L 15/225* (2013.01); *A61L 17/10* (2013.01)
USPC ............................................... 514/54; 514/62

(58) Field of Classification Search
None
See application file for complete search history.

(56) References Cited

U.S. PATENT DOCUMENTS

| 3,697,652 A | 10/1972 | Rovati et al. |
| 4,216,204 A | 8/1980 | Robertson |

(Continued)

FOREIGN PATENT DOCUMENTS

| EP | 0509120 A1 | 10/1992 |
| GB | 2317109 A | 3/1998 |
| WO | 2004/034980 A2 | 4/2004 |

OTHER PUBLICATIONS

Padgett, Arthritis, internet article, www.csa.com, released Jun. 1999.*

(Continued)

*Primary Examiner* — Layla Bland
(74) *Attorney, Agent, or Firm* — Sutherland Asbill & Brennan LLP

(57) ABSTRACT

The present invention provides a composition, and a method of use thereof, for treating connective tissue damage in man and in animals, which comprises a therapeutically effective amount of chondroitin sulfate, N-acetyl D-glucosamine, and hyaluronan (hyaluronic acid). Particularly, the present invention provides a composition, and a method of use thereof, for treating connective tissue damage including, but not limited to, arthritic disease, osteoarthritis, rheumatoid arthritis, osterochondrosis dessicans, cartilage damage, joint injury, joint inflammation, joint synovitis, degenerative joint disease (DJD), post surgical DJD, traumatic injury, fracture, tendon damage, ligament damage, skeletal damage, musculoskeletal damage, fiber damage, adipose tissue damage, blood cell damage, and plasma damage. Compositions for delivery of the present invention include those for parenteral, oral, and transmucosal delivery and for direct surgical placement onto the affected tissues.

20 Claims, No Drawings

(56) References Cited

U.S. PATENT DOCUMENTS

| | | | |
|---|---|---|---|
| 4,782,046 | A | 11/1988 | Brown et al. |
| 4,801,619 | A | 1/1989 | Lindblad |
| 4,808,576 | A | 2/1989 | Schultz et al. |
| 4,837,024 | A | 6/1989 | Michaeli |
| 5,141,928 | A | 8/1992 | Goldman |
| 5,364,845 | A | 11/1994 | Henderson |
| 5,442,053 | A | 8/1995 | della Valle et al. |
| 5,466,823 | A | 11/1995 | Talley et al. |
| 5,498,606 | A | 3/1996 | Soll et al. |
| 5,587,363 | A | 12/1996 | Henderson |
| 5,756,529 | A | 5/1998 | Isakson et al. |
| 5,840,715 | A | 11/1998 | Florio |
| 5,916,565 | A | 6/1999 | Rose et al. |
| 5,929,050 | A | 7/1999 | Petito |
| 6,127,356 | A | 10/2000 | Crapo et al. |
| 6,271,213 | B1 | 8/2001 | Henderson et al. |
| 6,432,929 | B1 | 8/2002 | Stone |
| 6,492,349 | B1 | 12/2002 | Henderson |
| 6,583,123 | B2 | 6/2003 | Henderson et al. |
| 6,632,804 | B2 | 10/2003 | Ekanayake |
| 6,645,948 | B2 | 11/2003 | Petito et al. |
| 6,906,044 | B2 | 6/2005 | Hermido |
| 6,949,525 | B2 | 9/2005 | Hermida |
| 2003/0216348 | A1 | 11/2003 | Henderson et al. |
| 2004/0253212 | A1 | 12/2004 | Koiwai et al. |
| 2006/0045872 | A1 | 3/2006 | Miguel et al. |

OTHER PUBLICATIONS

Schultz et al. Arthritis Research vol. 2, No. 6, 433-436, Aug. 10, 2000.*

Bassleer et al., 1998, "Stimulation of Proteglycan Production by Glucosamine Sulfate in Chondrocytes Isolated from Human Osteoarthritic Articular Cartilage in Vitro," Osteoarthritis and Cartilage, vol. 6, pp. 427-434.

Bucci et al., 1994, "Glucosamine Salts and Chondroitin Sulfates," Townsend Letter for Doctors, pp. 52-54.

Capps et al., 1966, "Hexosamine Metabolism," Biochimica et Biophysica ACTA, 127:194-204.

Coleman et al., 1999, "Characterization of the Effect of High Molecular Weight Hyaluronan on Trans-Synovial Flow in Rabbit Knees," Journal of Physiology, 514.1, pp. 265-282.

Coleman et al., 1997, "Hyaluronan Secretion into the Synovial Cavity of Rabbit Knees and Comparison with Albumin Turnover," Journal of Physiology, 503.3, pp. 645-656.

Coleman et al., 2000, "Role of Hyaluronan Chain Length in Buffering Interstitial Flow Across Synovium in Rabbits," Journal of Physiology, 526.2, pp. 425-434.

Day et al., 2002, "Hyaluronan-Binding Proteins: Tying up the Giant," The Journal of Biological Chemistry, vol. 277, No. 7, pp. 4585-4588.

Dorna et al., 1998, "Effects of Oral and Intramuscular Use of Chondroitin Sulfate in Induced Equine Aseptic Arthritis."

Hinderlich et al., 2000, "Molecular Cloning and Characterization of Murine and Human N-acetylglucosamine Kinase," Eur. J. biochem., 267:3301-3308.

Johnson et al., 2001, "Chondroitin Sulfate," Continuing Education Module from the New Hope Institute of Retailing.

McIlwraith, "Traumatic Joint Injuries and Disease," http://www.equineortho.colostate.edu/questions/tjd.htm, Jun. 12, 2007.

Murray M.:"Glucosamine sulfate: effective osteoarthritis treatment." Amer. J. Nat. Med. Sep. 10-14, 1994

Sabaratnam et al., 2002, "Interactive Effect of Chondroitin Sulphate C and Hyaluronan on Fluid Movement Across Rabbit Synovium," Journal of Physiology, 540.1, pp. 271-284.

Schiavinato et al., 2002, "Comparison of the Effects of Intra-Articular Injections of Hyaluronan and Its Chemically Cross-Linked Derivative (Hylan G-F20) in Normal Rabbit Knee Joints," Clinical and Experimental Rheumatology, 20:445-454.

Shikhman et al., 2001, "N-Acetylglucosamine Prevents IL-1beta-Mediated Activation of Human Chondrocytes," The American Association of Immunologists.

Tersariol et al., 2002, "Proteinase Activity Regulation by Glycosaminoglycans," Brazilian Journal of Medical and Biological Research, 335:135-144.

Tesoriere et al., 1972, "Intestinal Absorption of Glucosamine and N-Acetylglucosamine," Experientia 28:770-1.

Todhunter et al., 1993, "Effects of Exercise and Polysulfated Glycosaminoglycan on Repair of Articular Cartilage Defects in the Equine Carpus," Journal of Orthopaedic Research, 11:782-795.

Heart et al., 2002, "Glucose Transport by Osmotic Shock and Vanadate is Impaired by Glucosamine," Biochem Biophys Res Commun; 292:308-11.

de Mattei et al., 2002, "High Doses of Glucosamine-HC1 have Detrimental Effects on Bovine Articular Cartilage Explants Cultured in vitro," Osteoarthritis-Cartilage.; 10(10):816-25.

Breborowicz et al., 1998, "The effect of N-acetylglucosamine as a substrate for in vitro synthesis of glycosaminoglycans by human peritoneal mesothelial cells and fibroblasts," Adv Perit Dial; 14:31-5.

Barclay et al., 1998, "Glucosamine," The annals of Pharmacotherapy, 32(5):574-579.

Bertone, 1996, "Infectious Arthritis," Joint Disease in the Horse, W.B. Sanders, pp. 397-409 (ISBN 0-7216-5135-6).

Vidal et al., 1978, Pharmacol. Res. Commun., 10:557-569.

Maini et al., 1995, "Aetiopathogenesis of Rheumatoid Arthritis, in Mechanisms and Modes of Rheumatoid Arthritis," Academic Press Ltd., pp. 25-46.

Hesse, Cell Tissue Res (1987) 248:589-593.

* cited by examiner

COMPOSITION AND METHOD FOR TREATING CONNECTIVE TISSUE DAMAGE

CROSS-REFERENCE TO RELATED APPLICATIONS

This patent application is a continuation of U.S. application Ser. No. 11/766,510, filed Jun. 21, 2007, which claims continuation-in-part priority to co-pending U.S. application Ser. No. 11/015,137, filed on Dec. 17, 2004, and U.S. application Ser. No. 11/105,163, filed on Apr. 13, 2005, both of which claim continuation-in-part priority to U.S. application Ser. No. 10/686,918, filed on Oct. 16, 2003, issued as U.S. Pat. No. 6,979,679, which claims priority to U.S. Provisional Application Ser. No. 60/419,009, filed on Oct. 16, 2002 and U.S. Provisional Application Ser. No. 60/487,681, filed on Jul. 16, 2003, the entire contents of which are all incorporated by reference herein.

FIELD OF INVENTION

The present invention is generally directed to compositions, and methods of use thereof, for treating connective tissue damage in man and in animals. More particularly, the present invention provides a proteoglycan composition for use in treating, for example, osteoarthritis, rheumatoid arthritis, osteochondrosis dessicans, cartilage damage, joint inflammation, joint synovitis, joint injuries, degenerative joint disease, post surgical degenerative joint disease, traumatic injuries, fractures, tendon damage, ligament damage, skeletal damage, musculoskeletal damage, bone damage, fiber damage, adipose tissue damage, blood cell damage, and plasma damage.

BACKGROUND OF THE INVENTION

The four primary types of vertebrate tissues are epithelial tissue, muscle tissue, nerve tissue, and connective tissue. Connective tissues are typically involved in structure and support, and are usually derived from mesoderm cells. Connective tissue is widespread in the body, and as the name implies, it primarily serves a connecting function to bind or strengthen organs or other tissues. It also functions inside the body to divide and compartmentalize other tissue structures.

In vertebrates, the most common type of connective tissue is loose connective tissue. Loose connective tissue holds organs in place and attaches epithelial tissue to other underlying tissues. Loose connective tissue is named based on the "weave" of its constituent fibers. There are three main component types of loose connective tissue: collagenous fibers, elastic fibers, and reticular fibers. Collagenous fibers are made of collagen and consist of bundles of fibrils that are coils of collagen molecules. Elastic fibers are made of elastin and are stretchable. Reticular fibers join connective tissues to other tissues. Loose connective tissue also includes adipose tissue that stores fat.

Another type of connective tissue is fibrous connective tissue, which is found in tendons and ligaments. Fibrous connective tissue is composed of large amounts of closely packed collagenous fibers. Cartilage is a form of fibrous connective tissue that is composed of closely packed collageous fibers in a rubbery gelatinous substance called chondrin. The skeletons of sharks are composed of cartilage. Cartilage also provides flexible support for certain structures in humans including the nose, trachea, ears, and articulating joints, for example.

Bone and blood are two other specialized connective tissues. Bone is a type of mineralized connective tissue that contains collagen and calcium phosphate, a mineral crystal. Calcium phosphate gives bone its firmness. Blood is also considered a type of connective tissue. Even though it has a different function in comparison to other connective tissues it does have an extracellular matrix. The matrix is the plasma and erythrocytes, leukocytes and platelets are suspended in the plasma.

The connective tissues of humans and animals are constantly subjected to stresses and strains from mechanical forces and from diseases that can result in afflictions, such as arthritis, joint inflammation stiffness and connective tissue injuries such as tendonitis, bursitis, strained or torn ligaments and tendons and the like. Indeed, connective tissue afflictions are quite common, presently affecting millions of Americans. Further, such afflictions can be not only painful but, in their extreme, debilitating.

Arthritic diseases, characterized by pain, inflammation and stiffness of the joints leading to reduced range of mobility, are due to the degradation of connective tissue (mainly cartilage) in joints. Such diseases particularly affect weight-bearing joints such as the hips, knees, spine, ankles and feet and those joints with frequent movement such as hands, arms and neck. For instance, osteoarthritis (OA) in particular is a degenerative disease of the joint cartilage resulting in narrowing of the joint space and changes in the underlying bone (Barclay, et al., The Annals of Pharmacotherapy, (May, 1998) 32: 574-79). Osteoarthritis is the most common form of arthritis and it affects approximately one in ten people in North America. Osteoarthritis is not limited to humans, but occurs in other mammals such as horses, dogs, cats, mice and guinea pigs as well, making osteoarthritis one of the most common sources of chronic pain seen by veterinarians.

In humans, rheumatoid arthritis (RA) is a connective tissue disease that has some similar symptoms to osteoarthritis. Rheumatoid arthritis is among the most debilitating of all forms of arthritis, causing joints to ache and throb and eventually become deformed. Sometimes these symptoms make even the simplest daily activities difficult to manage.

The exact cause of rheumatoid arthritis is unknown, however, it is believed to be an autoimmune disease (Maini, et al., Aetiopathogenesis of Rheumatoid Arthritis. in Mechanisms and Modes of Rheumatoid Arthritis, (1995) Academic Press Ltd. pp. 25-46), in which the immune system attacks body tissues, e.g., the synovium, as if they were foreign invaders, culminating in inflammatory and destructive responses in joints as well as other tissues. It has also been postulated that rheumatoid arthritis is triggered by an infection, possibly a virus or bacterium in people with an inherited susceptibility. Some researchers also believe that hormones may be involved in the development of rheumatoid arthritis.

As with other forms of arthritis, rheumatoid arthritis involves inflammation of the joints. In rheumatoid arthritis, white blood cells, whose usual job is to attack unwanted invaders, such as bacteria and viruses, move from the bloodstream into the synovium. Here, these blood cells appear to play an important role in causing the synovial membrane to become inflamed (synovitis). This inflammation results in the release of proteins that, over months or years, cause thickening of the synovium. These proteins can also damage cartilage, bone, tendons and ligaments. Gradually, the joint loses its shape and alignment and eventually, it may be destroyed.

Under normal conditions, the body maintains the synovial joint in state of homeostasis through a variety of complex hormonal and mechanical feedback mechanisms. Several types of insult or injury can upset the delicate homeostatic balance. For example, repeated trauma or stress (slow chronic insult) to the joint during everyday use, e.g., athletic training or performance, is often the inciting cause of joint inflammation and loss of homeostasis. Initially, such stress results in only soft tissue inflammation in the form of synovitis or capsulitis (e.g., traumatic synovitis). Cartilage damage may or may not initially be present in the early stages of stress related injury or inflammation. However, the release of inflammatory mediators into the joint such as prostaglandins, cytokines, lysosomal enzymes and free radicals can lead to damage of articular cartilage and can cause cartilage degradation and leading to development of degenerative joint disease (DJD).

A second type of insult or injury, the osteochondral defect, e.g., a chip fracture, is often associated with an acute mechanical failure or traumatic injury, e.g., an acute racing or training injury, although, such a fracture can be due to secondary complications associated with chronic DJD. Under this scenario, the lesion often starts as a traumatically induced defect in the articular cartilage. This may occur as a fragmentation of the original tissue from the joint margins or other defect which compromises the surface and integrity of the articular cartilage. Exposure of the supporting subchondral bone to synovial fluid and the intermittent pressures of the synovial fluid generated by repeated joint movement (repeated stress and trauma of training or racing) can lead to progressive subchondral bone sclerosis and eventual dislodging of the chip or bone fragment. Left untreated, the resulting damage often becomes progressive and DJD results (see, e.g., Nixon et al., "EQUINE FRACTURE REPAIR", W. B. Saunders Co., 1996 (ISBN 0-7216-6754-6)).

Under either scenario, once compromised, the damage to articular cartilage is usually permanent. In general, once damaged, therapy is normally directed at limiting or reducing joint inflammation, limiting the release of inflammatory mediators, removal of the inciting cause (e.g., the chip) and replacement of synovial fluid components. These measures are combined with a period of rest to allow for healing and fibrocartilage deposition at the affected area. The long term therapeutic objective is directed at slowing the progression of degenerative processes and controlling the clinical signs of DJD. Prevention is often aimed at limiting joint inflammation before damage to cartilage occurs and in providing proper nutritional support.

The treatment of connective tissue afflictions can be quite problematic. A simple decrease in the stress to which the connective tissue is subjected is often not an option, especially in the case of athletes and animals such as race horses. Consequently, treatment is often directed at controlling the symptoms of the afflictions and not their causes, regardless of the stage of the degenerative process. Presently, steroids, such as corticosteroids and NSAIDs, are widely used for the treatment of these ailments (Vidal, et al., Pharmocol. Res. Commun., 10:557-569 (1978)). However, drugs such as these, which inhibit the body's own natural healing processes, may lead to further deterioration of the connective tissue.

Connective tissue, for example articular cartilage, is naturally equipped to attempt to repair itself by manufacturing and remodeling prodigious amounts of collagen and proteoglycans (PGs). This ongoing process is placed under stress when an injury occurs. In such cases, the production of connective tissue matrix (collagen and proteoglycans) can double or triple over normal levels, thereby increasing the demand for the building blocks of both collagens and proteoglycans. The building blocks for collagen are amino acids, especially proline, glycine and lysine. Proteoglycans are large and complex macromolecules comprised mainly of long chains of modified sugars called glycosaminoglycans (GAGs) or mucopolysaccharides. The terms glycosaminoglycans and mucopolysaccharides are understood in the art to be interchangeable. Due to their dense negative ion content, proteoglycans molecules are able to attract and retain water within the cartilage formation specifically for lubrication. Proteoglycans provide the unique mechanical properties for flexibility, resiliency, and resistance to and recovery under compressive forces.

Glucosaminoglycans are polysaccharides which occur widely in the animal kingdom. Glucosaminoglycans that are present in the tissues of vertebrate animals have mainly a linear structure which is repetition of a disaccharide units composed of two monosaccharides. Five kinds of glucosaminoglycans are found in the tissues and fluids of vertebrates: chondroitin sulfates, keratin sulfates, dermatan sulfates, heparin sulfates, and hyaluronic acid.

Proteoglycans and collagen are the chief structural elements of all connective tissues. Their synthesis is essential for proper maintenance and repair of connective tissues. In vitro, the introduction of glucosamine, a key precursor for GAGs, has been demonstrated to increase the synthesis of collagen and GAGs in fibroblasts. In vivo, topical application of glucosamine has enhanced wound healing. Glucosamine has also exhibited reproducible improvement in symptoms and cartilage integrity in humans with osteoarthritis (L. Bucci, Nutritional Supplement Advisor, July 1992)).

The major proteoglycans found in cartilage are chondroitin sulfate, dermatan sulfate, keratan sulfate and hyaluronic acid (also known as hyaluronan or HA). Heparin sulfate is also a proteoglycan, although it is not a component of articular cartilage. Newer names for proteoglycans sometime reference function of the core protein within the molecule found in chondroitin sulfate and keratin sulfate, e.g., aggregan, a large proteoglycan aggregates with hyaluronin, or reference location (e.g., decorin (dermatan sulfate), which decorates type I collagen fibrils), or reference primary structure, biglycan which has two glysoaminoglycan chains. Chondrocytes are active cells within the cartilage matrix, which manufacture new collagen and proteoglycan molecules while excreting enzymes, which aid in removal of damaged cartilage and proteoglycans.

Chondroitin sulfate is broken down into sulfate disaccharides and N-acetyl galactosamine. D-Glucuronic acid is a key substrate comprising one half of the hyaluronan molecule, the other being N-acetyl D-glucosamine. Chondroitin sulfate, as CS4 and CS6 within the body, is thought to be an essential glycosaminoglycan which binds water to the articular cartilage matrix and is necessary for the formation of proteoglycans.

In particular, chondroitin sulfate is a long hydrophilic chain of repeating sugars. This glycosaminoglycan binds to proteoglycan molecules aiding in water and nutrient transportation within the articular cartilage. Chondroitin in its sulfate form includes galactosamine, a primary substrate of hylauronan and a disaccharide pathway for proteoglycan synthesis secondary to the hexosamine pathways utilised for glycosaminoglycan production. Chondroitin sulfate chains comprise the space formation of the cartilage matrix and integral parts of the proteoglycan molecule. Chondroitin stimulates the production of proteoglycans, glycosaminoglycans, and collagen, which are the building blocks of healthy cartilage. Chondroitin sulfate also inhibits the secretion of degenerative enzymes by the chondrocytes within articular cartilage. Chondroitin sulfates are non-toxic and work synergistically with glucosamine to hydrate and repair articular cartilage.

Hylauronan is an integral part of both synovial fluid and articular cartilage. Within the articular cartilage, hylauronan provides viscoelastic properties allowing ease of motion between opposing surfaces and increasing compressive resistance. Within the synovium, hylauronan, as a component of synovial fluid, provides an effective barrier regulating the introduction of plasma components. Under normal conditions, the body will synthesize sufficient amounts of base components to maintain and grow healthy articular cartilage, while limiting the production and release of destructive proteinases, inflammatory mediators and catabolic enzymes.

Glucosamine, as glucosamine 5-phosphate, is naturally occurring within the body and is a component in the biosynthesis of glycosaminoglycans, proteoglycans, hyaluronan, and collagen. Glucosamine is available in exogenous forms, glucosamine sulfate sodium, glucosamine hydrochloride and N-acetyl D-glucosamine. N-acetyl D-glucosamine is also a derivative of glucose obtained by chemical hydrolysis of chitin. This polysaccharide is readily soluble in water and extremely bioavailable. N-acetyl D-glucosamine binds to glucuronic acid as well as galactose making it a precursor to hyaluronic acid, keratan-sulfate and chondroitin sulfate. This unique derivative aids in proteoglycan, collagen and glycosaminoglycan production. N-acetyl D-glucosamine has also been shown to aid in the healing of soft tissue injury.

There have been countless therapeutic approaches for management of joint disease, providing nutritional supplementation of metabolic precursors to the diet to aid in the biosynthesis of proteoglycans, GAG's, hyaluronan, and collagen (see, U.S. Pat. Nos. 5,364,845 and 5,587,363). Numerous other disclosures also suggest the introduction of nutritional supplements as therapy for the treatment of connective tissues. For instance, U.S. Pat. No. 3,683,076 to Rovati et al. teaches that glucosamine sulfates are useful to treat arthritic conditions. U.S. Pat. No. 3,697,652 to Rovati et al. discloses that N-acetyl glucosamine can be used to treat degenerative afflictions of the joints. U.S. Pat. Nos. 5,364,845, 5,587,363, 6,492,349, 6,271,213, and 6,583,123 to Henderson et al. teach that glucosamine, chondroitin, manganese, and/or S-Adenosylmethionine (SAM) are used to protect and repair connective tissue. U.S. Pat. No. 6,632,804 to Ekanauake teaches that ferrous ion and an ascorbate, and glucodamine derivative are useful in treating osteoarthritis. U.S. Pat. No. 6,645,948 to Prtito et al. teaches a nutritional composition for treating connective tissue including a glucosamine salt, chondroitin sulfate, collagen and sodium hyaluronate.

In U.S. Pat. No. 5,840,715 to Florio, N-acetyl glucosamine sulfate, chondroitin sulfate, gamma linolenic acid ercosapentaenoic acid and docosahexaneoic acid, and manganese aspartate are combined to treat arthritis symptoms. U.S. Pat. No. 5,916,565 to Rose et al. teaches a composition comprised of D-glucosamine hydrochloride, chondroitin sulfate, cayenne, ginger, turmeric, yucca, Devil's Claw, nettle leaf, Black Cohosh, alfalfa, and celery seeds to repair and maintain damaged tissues in joints of vertebrates. In U.S. Pat. No. 5,922,692, Marino discloses that glucosamine sulfate and chondroitin sulfate can be added to foodstuffs. Additional related art discloses pharmaceutical compositions and methods for the treatment of connective tissue in humans and animals, such as U.S. Pat. Nos. 4,216,204, 4,782,046, 4,808,576, 4,837,024, 5,141,928, 5,840,715, 5,442,053, and 5,929,050.

While all the above references have been described as being effective for their intended use, there remains a need in the art for a therapeutic composition which demonstrates enhanced effectiveness in the treatment of connective tissues, exhibit other improved beneficial properties, and provides even wider applications in the modes of administration. The present invention meets these needs at least in part.

SUMMARY OF THE INVENTION

The present invention provides a composition which demonstrates enhanced effectiveness in the prevention or treatment of connective tissue damage. In one of the preferred embodiments of the invention, the composition comprises a therapeutically effective amount of chondroitin sulfate, glucosamine, and hyaluronan (hyaluronic acid). In the joint, for example, chondroitin sulfate acts to stimulate the production of proteoglycans, glycosaminoglycans, and collagen, inhibits degenerative enzymes excreted by the chondrocytes, and synoviocytes, and aids in nutrient transportation within the synovial fluid. Glucosamine, e.g., the presently preferred N-acetyl D-glucosamine, increases the synoviocyte and chondrocyte production and subsequent availability of endogenous hyaluronan by the direct in situ inclusion of its prime substrates galactosamine (through chondroitin sulfate assimilation) and N-acetyl D-glucosamine. The exogenous hyaluronan acts to replace depleted endogenous hyaluronan and to lubricate and coat healthy as well as damaged articular tissue during the reparative process. The above modes of action are believed accurate, however, the claimed uses of the present compositions is not limited to such hypothesized mechanisms of activity for achieving efficacy.

In one preferred embodiment, the chondroitin sulfate comprised in the composition is preferably chondroitin 4-sulfate (CS4), chondroitin 6-sulfate (CS6), or a mixture of both CS4 and CS6. A therapeutically effective amount of chondroitin sulfate and N-acetyl D-glucosamine is preferably from between about 0.5 grams to about 1.5 grams of per unit dose, respectively, and the therapeutically effective amount of hyaluronan is preferably from about 10 mg to about 50 mg per unit dose.

In another preferred embodiment, the compositions provided herein are preferably in sterile solution, suspension, or other pharmaceutically acceptable formulations. The composition provided herein can be applied directly to the affected connective tissue, or preferably, is adapted for intra-articular and/or systemic or parenteral administration. Systemic administrations can include, but are not limited to, intramuscular, intravenous or subcutaneous injection or via direct adsorption into the bloodstream via non-gastrointestinal transmucosal, e.g., sublingual administration.

In one embodiment, the compositions provided herein are adapted for direct injection into a target connective tissue, e.g., a tendon, a ligament or bone, or they may be adapted for direct application to the target tissue as in, for example, a gel or paste-like material to enhance and/or prolong contact with the target tissue. In another embodiment, the compositions of the invention are adapted for transmucosal delivery for direct adsorption into the bloodstream such as by sublingual or other oral transmucosal delivery. It is contemplated by certain embodiments of the invention that the trasnsmucosal delivery can include any mucosal tissue that provides a mucosal surface area for direct adsorption into the blood stream and that does not subject the compositions of the invention to digestion and/or other alteration via gastric or intestinal enzymes. The compositions can be provided as liquids or semi-solids for direct application to the desired mucosal tissue. The compositions can be formulated into any of a variety of presentations designed to enhance and/or prolong contact with the desired mucosal tissue to promote adsorption into the bloodstream. For example, the compositions can be incorporated into a dissolvable or biodegradable film for placement e.g., under the tongue or as an oral or nasal spray or other presentation designed to enhance and/or prolong contact with the mucosa of the oropharnyx or other target mucosal tissue.

In yet another preferred embodiment, the composition provided herewith is attached to a sheet of material adapted for implantation onto or between tissues of a mammalian body. Preferably, the composition is impregnated into a polymeric gauze-like material or coated onto a gauze-like material or joined to the material by adhesion and/or capillary action. The material onto which the composition is attached may be either a permanent implant or it may be biodegradable. In yet another preferred embodiment, the composition provided herewith is attached to a bandage or other surgical materials, including, but not limited to, surgical suture material, surgical staple, or a device such as a buckle.

The composition provided herewith further may optionally comprise one or more other therapeutic agents, including, but not limited to, synthetic and non-synthetic corticosteroid agents, nonsteroidal anti-inflammatory drugs, antirheumatics, immunoregulators, immunosuppressant, articular function augmenters, interleukin production inhibitors, grow factor, or stem cells having therapeutic effects. Any drugs, agents, compounds, known and/or to be developed, showing any desired therapeutic effects are within the scope of this invention. In other embodiments, the invention may specifically exclude one or more of the above therapeutic agents.

The present invention provides a composition which demonstrates enhanced effectiveness promoting healthy growth of connective tissue and in the treatment of connective tissue damage. As used herein, the term "connective tissue" refers to loose, dense regular, and elastic connective tissues. The loose connective tissues comprises constituent fibers including, but not limited to, collagenous fibers, elastic fibers, reticular fibers. The loose connective tissue also refers to an adipose tissue. The dense regular connective tissues include, but are not limited to, tendons, ligaments, cartilage, skeleton, and other fibrous connective tissues. The connective tissues used herein also refer to blood.

The composition of the present invention can be used in the prevention or treatment of connective tissue damage, which includes any primary or secondary diseases or injuries to the connective tissues in humans or animals. Such diseases or injuries include, but are not limited to, arthritic diseases, osteoarthritis (OA), rheumatoid arthritis (RA), osteochondrosis dessicans (OCD), cartilage damage, joint injuries, joint inflammation, joint synovitis, degenerative joint disease (DJD), post surgical DJD, traumatic injuries, fractures, tendon damage, ligament damage, skeletal damage, musculoskeletal damage, bone damage, fiber damage, adipose tissue damage, blood cell damage, and plasma damage.

The present invention further provides a method for preventing or treating connective tissue damage in humans or in animals comprising administering to a man or animal in need thereof, a therapeutically effective amount of a composition comprising chondroitin sulfate, glucosamine, e.g., N-acetyl D-glucosamine, and hyaluronan. In one preferred embodiment, the composition is directly applied to the affected connective tissues. In another preferred embodiment, the composition provided herein is adapted for intra-articular or systemic or parenteral administration. Systemic administrations can include, but are not limited to, intramuscular, intravenous, or subcutaneous injection and transmucosal administration, e.g., sublingual administration. The connective tissue damage referred to herein includes any primary or secondary diseases or injuries to the connective tissues in humans or animals.

The present invention further provides a kit comprising one or more containers comprising the composition provided herein, which comprises a therapeutically effective amount of chondroitin sulfate, glucosamine, e.g., N-acetyl D-glucosamine, and hyaluronan, and instructions for use of the composition for preventing or treating connective tissue damage in man or in animals. The invention of the kit provided herein can also include, or specifically exclude, other separate containers for other drugs, agents, compounds having desired therapeutic effects. Examples for these drugs, agents and compounds include, but are not limited to, synthetic and non-synthetic corticosteroid agents, nonsteroidal anti-inflammatory drugs (NSAIDS), antirheumatics (e.g., disease modifying antirheumatic drugs (DMARDS) such as tissue necrosis factor blockers (TNFs)), immunoregulators, immunosuppressant, articular function augmenters, interleukin production inhibitors, growth factors such as cartilage derived morphogenic proteins (e.g., CDMP-2), bone morphogenic proteins, and stem cells and/or progenitor cells having therapeutic effects.

The composition provided in the kit can be stored in any suitable container, including but not limited to, syringes and vials, and in various dosage units. Preferably, the dosages for chondroitin sulfate and the presently preferred glucoasamine, N-acetyl D-glucosamine, are from between about 0.5 grams to about 1.5 grams per unit dose, respectively, and the dosage for hyaluronan is from about 10 mg to about 50 mg per unit dose. The chondroitin sulfate, N-acetyl D-glucosamine, and hyaluronan provided in the kit are formulated in sterile solutions, suspensions, or any pharmaceutically acceptable formulations, and stored in suitable containers, separately or in combination, in various dosage units. Preferably, the containers in the kit containing the compositions provided herein are disposable.

In yet another preferred embodiment, the kit provided herein contains a sheet of material adapted for implantation onto or between tissues of a human body and with the composition attached thereon. Preferably, the sheet of material is in the form of an impregnatable material and is dissolvable and biodegradable. Furthermore, the kit provided herein includes instructions indicating a method of use of the composition for treating any primary or secondary diseases or injuries to the connective tissues in humans or animals.

DETAILED DESCRIPTION OF THE INVENTION

Additional objects, advantages and other novel features of the invention will be set forth in part in the description that follows and in part will become apparent to those skilled in the art upon examination of the foregoing or may be learned with the practice of the invention. Additionally, throughout this document, various publications and patents have been cited, the contents of which are incorporated herein by reference in their entirety.

Set forth in greater detail below are specific details related to a composition which demonstrates enhanced effectiveness in the treatment of connective tissue damage. The composition provided herein comprises a therapeutically effective amount of chondroitin sulfate, a suitable glucosamine derivative, e.g., N-acetyl D-glucosamine, and a suitable hyaluronan (hyaluronic acid). It is believed, that chondroitin sulfate acts to stimulate the production of proteoglycans, glycosaminoglycans, and collagen, inhibits degenerative enzymes excreted by the chondrocytes, and synoviocytes, and aids in nutrient transportation within the synovial fluid. It is believed that glucosamine derivatives, e.g. N-acetyl D-glucosamine, increase the synoviocyte and chondrocyte production and subsequent availability of endogenous hyaluronan by the direct in situ inclusion of its prime substrates galactosamine (through chondroitin sulfate assimilation) and N-acetyl D-glucosamine. It is further believed that the exogenous hyaluronan acts to replace depleted endogenous HA and to lubricate and coat healthy as well as damaged articular tissue during the reparative process. The examples and proposed mechanisms of action set forth herein are in no way intended to limit the scope of the invention. Those of skill in the art will realize that, given the teachings provided herein, many variations of the compositions, methods of use thereof, are possible that will fall within the scope of the of the invention.

The compositions of the invention provide a unique mixture comprised of the naturally occurring glucosaminoglycans: chondroitin sulfates CS4 and CS6, a suitable hyaluronan (hyaluronic acid) and a suitable glucosamine derivative, e.g., N-acetyl D-glucosamine. It can be appreciated that, depending upon the target connective tissue, the suitable glucosamine derivative can be selected from any of the glucosamine derivatives including, but not limited to, glucosamine 5-phosphate, glucosamine sulfate sodium, glucosamine hydrochloride, N-acetyl D-glucosamine and mixtures thereof.

Chondroitin sulfates are one important component of certain embodiments of the compositions of the invention. In general, chondroitin sulfates are widely found in the connective tissues of animals in two forms of repeating disaccharides of D-glucoronic acid and N-acetyl galactosamine: CS4 sulfate where n-acetyl galactosamine holds an ester sulfate in its CS4 position or CS6 sulfate where the ester sulfate is in the CS6 position. Both CS4 and CS6 chondroitin sulfate function in the articular matrix as a major constituent. Chondroitin sulfates contribute to keep the cartilage matrix's normal characteristics through the increase of the glucosaminoglycan pool used by the chondrocytes for proteoglycan synthesis, as well as slowing down the inflammatory process acting directly on the enzymes inhibiting the compliment cascade and by exhibiting anti-prostoglandin activity.

Another important component of certain embodiments of the compositions of the invention, hyaluronan and its salt (e.g., sodium hyaluronate), is a natural constituent of connective tissues and synovial fluid composed of repeating disaccharide units each consisting of D-glucoranic acid and N-acetyl D-glucosamine. Within the joint capsule, the surface of articular cartilage is covered by a thin layer of sodium hyaluronate. It specifically interacts with cartilage proteoglycans to form a stabile aggregate. Within the synovial fluid it confers viscal elasticity as well as lubricating properties. Hyaluronan aids in providing nourishment and waste removal from the articular matrix. It also provides biochemical activity to help prevent excess fibrous tissue from forming in the cartilage matrix.

In addition, N-acetyl D-glucosamine is also important to certain embodiments of the compositions of the invention, and is a key compound for cartilage matrix synthesis as it enhances chondrocyte synthesis of glucosaminoglycans. N-acetyl D-glucosamine also possesses the ability to enhance synthesis of key components of synovial fluid by feeding both reactions necessary for the production of hyaluronan as well as for proteoglycans. Therefore, by replacing specific glucosaminoglycans lost by the invasion of the diarthrodial joint during surgery and also providing the key molecules to enhance and promote the restoration of normal hyaluronan and proteoglycan synthesis, the physician or veterinarian can be assured of the composition's capability to protect the joint as well as to aid in the healing process.

As used herein, the chondroitin sulfate comprised in the composition is preferably chondroitin 4-sulfate (CS4), chondroitin 6-sulfate (CS6), or a mixture of both CS4 and CS6. The therapeutically effective amount of chondroitin sulfate and N-acetyl D-glucosamine is preferably from between about 0.5 grams to about 1.5 grams of per unit dose, respectively, and the therapeutically effective amount of hyaluronan is preferably from about 10 mg to about 50 mg per unit dose. In one embodiment, the therapeutically effective amount comprises about 1 gram of CS4 chondroitin sulfate, or about 1 gram of CS6 chondroitin sulfate or about 1 gram of a mixture of CS4 and CS6 chondroitin sulfate per unit dose. In another embodiment, the therapeutically effective amount of chondroitin sulfate is about 1 gram of chondroitin sulfate comprised of about 40% CS4 chondroitin sulfate and about 60% CS6 chondroitin sulfate.

An especially preferred therapeutic amount of N-acetyl D-glucosamine is about 1 gram of N-acetyl D-glucosamine per unit dose of the composition. Presently preferred therapeutic amounts of hyaluronan include from about 10 mg to about 50 mg of hyaluronan per unit dose of the composition. An especially preferred therapeutic amount of hyaluronan is from about 20 to about 40 mg of hyaluronan per unit dose of the composition.

It can be appreciated by one of skill in the art that the hyaluronan can be selected from among any of a number of commercially available sources, such as commercially available sodium hyaluronate, and can include alternative salts and metabolic precursors or metabolites thereof. Likewise there are numerous commercially available sources of N-acetyl D-glucosamine and chondroitin sulfate and various alternative salts or metabolic precursors or metabolites thereof that are available for use in the compositions set forth herein.

Another presently preferred embodiment of the invention provides a composition comprising a sterile solution or suspension comprising about 1 gram of chondroitin sulfate as a mixture of about 40% CS4 and 60% CS6 chondroitin sulfate; about 1 gram of N-acetyl D-glucosamine; and about 20-40 mg but especially about 30 mg of hyaluronan (e.g., sodium hyaluronate) per unit dose of the composition.

One example of a preferred embodiment of the invention comprises a 10 ml unit dose of the composition. The composition is made as follows. One gram of chondroitin sulfate powder is admixed with one gram of N-acetyl D-glucosamine powder. These powders are weighed, admixed and 2 ml of a 10 mg/ml solution of sodium hyaluronate is added to the powder mixture. The resultant mixture of chondroitin sulfate, N-acetyl D-glucosamine and sodium hyaluronate is qs with approximately 10 ml of bacteriostatic water to achieve a final volume of 10 ml. The final concentration of chondroitin sulfate in the composition is 0.1 gram/ml or 10%. The final concentration of N-acetyl D-glucosamine in the composition is 0.1 gram/ml or 10% and the final concentration of sodium hyaluronate in the composition is 0.2 nil/ml or 20%.

One presently preferred embodiment of the invention provides a composition consisting essentially of therapeutic amounts of chondroitin sulfate, N-acetyl D-glucosamine; and hyaluronan. The composition may specifically exclude other therapeutic agents, such as analgesics, or may specifically include other therapeutic agents, such as immunosupressants or bactericides In another embodiment the invention provides a composition comprising therapeutically effective amounts of chondroitin sulfate, N-acetyl D-glucosamine, and hyaluronan wherein the molecular weight per unit dose of the composition is from between about 450,000 Daltons to about 1,600,000 Daltons. In yet another embodiment, the invention provides a composition which comprises therapeutically effective amounts of chondroitin sulfate, N-acetyl D-glucosamine, and hyaluronan wherein the molecular weight per unit dose of the composition is from between about 500,000 Daltons to about 1,400,000 Daltons. In yet another embodiment the invention provides a composition which comprises therapeutic amounts of chondroitin sulfate, N-acetyl D-glucosamine, and hyaluronan wherein the molecular weight per unit dose of the composition is from between about 550,000 Daltons to about 700,000 Daltons, but is especially about 600,000 Daltons.

In a preferred embodiment the invention provides a composition which comprises therapeutic amounts of chondroitin sulfate, N-acetyl D-glucosamine, and hyaluronan wherein the molecular weight per unit dose of the composition is greater than about 450,000 Daltons. In another embodiment, the invention provides a composition which comprises therapeutic amounts of chondroitin sulfate, N-acetyl D-glucosamine, and hyaluronan wherein the molecular weight per unit dose of the composition is greater than about 550,000 Daltons.

Preparation of the composition provided herein may be made by conventional methods. For example, to prepare the compositions of the invention, the above-described ingredients are combined as the active ingredient in intimate admixture with or without a suitable carrier according to conventional compounding techniques. This carrier may take a wide variety of forms depending upon the form of preparation desired for administration, e.g., oral, sublingual, nasal, guttural, rectal, transdermal or parenteral.

In preparing the compositions in oral dosage form, any usual pharmaceutical medium may be employed. For oral liquid preparations (e.g., suspensions, elixirs, and solutions), media containing for example, water, oils, alcohols, flavoring agents, preservatives, coloring agents and the like may be used. Carriers such as starches, sugars, diluents, granulating agents, lubricants, binders, disintegrating agents, and the like may be used to prepare oral solids (e.g., powders, capsules, pills, caplets, tablets, microencapsulated granules, microtablets, coated granules and lozenges). Capsules or tablets are a preferred oral dosage form. Controlled release forms may also be used. Because of their ease in administration, lozenges, tablets, pills, caplets, and capsules represent the most advantageous oral dosage unit form, in which case solid pharmaceutical carriers are obviously employed. If desired, tablets may be sugar coated or enteric coated by standard techniques. The compositions of the present invention may be in the form of one or more of these oral dosage forms, i.e., a single dosage may be in multiple forms.

The composition of the present invention can also be provided in a bioavailability enhancing, non-gastrointestinal transmucosal delivery form, such as for sublingual or intranasal delivery. Detailed discussion on sublingual absorption and its benefits for drug delivery are provided by Lea (Sublingual Absorption, Positive Health) and Tolson (Bulk Nutrition, HPBCD Basics) (the entire contents of these articles are incorporated by reference herewith). The transmucosal formulations may include thickening carriers or polymers, such as in sprays, pastes, gels or dissolvable tablets or sheets, which prolong adherence of the composition to oral or nasal mucosal membranes.

In one embodiment, the composition of the invention can be formulated for transmucosal delivery into flavored oral paste comprising polyethylene glycol, flavorings, and stevioside 90% power. In another embodiment, the composition of the present invention can be formulated for transmucosal delivery into a hydroxypropyl cellulose (e.g., 1%)/propylene glycol gel. In yet another embodiment, the composition of the present invention can be formulated for transmucosal delivery into a hydroxyethyl cellulose (e.g., 1.75%)/glycerin (e.g., 20%)/propylene glycol (e.g., 30%) aqueous gel. In yet another embodiment, the composition of the present invention can be formulated into a hydroxyethyl cellulose (e.g., 2.5%) aqueous gel.

For parenteral products, the carrier will usually comprise sterile water, although other ingredients may be included, e.g., to aid solubility or for preservation purposes. Injectable suspensions may also be prepared, in which case appropriate liquid carriers, suspending agents, and the like may be employed.

In some preferred embodiments, the composition provided herein is preferably in sterile solution, suspension, or other pharmaceutically acceptable formulations. The composition provided herein can be applied directly to the affected connective tissue, or is adapted for intra-articular and/or systemic or parenteral administration. Systemic administrations can include, but are not limited to, intramuscular, intravenous or subcutaneous injection. Thus, in one embodiment, the compositions of the invention have been specially adapted for intra-articular use and/or parenteral (e.g., intravenous or intramuscular) are sterile solutions or suspensions comprised of therapeutic amounts of chondroitin sulfate, N-acetyl D-glucosamine, and hyaluronan. In addition to the aforementioned active agents, it can be appreciated by one of skill in the art that the compositions of the invention which are adapted for intra-articular use, and other therapeutic use can also comprise preservatives, pharmaceutically active carriers, excipients, stabilizers, buffers, antimicrobial growth inhibitors and the like, and the use of such is contemplated by the invention.

It is also contemplated that other formulations are possible and are within the scope of the invention, e.g., a powdered formulation suitable for reconstitution with a suitable injectable liquid or for addition to a pre-selected lavage fluid. In particular, it can be appreciated by one of skill in the art that the active agents of the compositions can be stored in a freeze dried or lyophilized state for reconstitution and use at a desired time.

In yet another preferred embodiment, the composition provided herewith is attached to an impregnated bolus or a sheet of material adapted for implantation directly onto or between connective tissues of a mammalian body, for example to prevent the formation of post-operative adhesions, e.g., scar tissue formation. Preferably, the composition is impregnated into an absorptive gauze-like material or coated onto the material or joined to the material by adhesion and/or capillary action to a mesh or gauze. The material onto which the composition is attached or absorbed may be either a permanent implant or it may be biodegradable. In one embodiment, the therapeutic composition is dispersed on or within a malleable material which can be shaped for insertion into diseased or excised tissue spaces. In yet another preferred embodiment, the composition provided herewith is attached to a bandage or other surgical materials, including but not limited to surgical suture material, surgical staple, or a device such as a buckle. Surgically implanted devices and sheet of materials having drugs/compositions attached thereon are disclosed in U.S. Pat. No. 6,534,693 (the entire contents of which is incorporated herein by reference).

It is contemplated by the invention that the compositions provided herein demonstrate enhanced effectiveness in the treatment of any primary and/or secondary damages and/or injuries to any connective tissues in humans and animals. Such diseases and/or injuries include, but are not limited to, arthritic diseases, osteoarthritis (OA), rheumatoid arthritis (RA), osteochondrosis dessicans (OCD), cartilage damage, joint injuries, joint inflammation, joint synovitis, degenerative joint disease (DJD), post surgical DJD, traumatic injuries, fractures, tendon damage, ligament damage, skeletal damage, musculoskeletal damage, bone damage, fiber damage, adipose tissue damage, blood cell damage, and plasma damage, and the like.

In one embodiment of the invention compositions and methods for treatment of rheumatoid arthritis (RA) are provided. Rheumatoid arthritis is thought to be a human autoimmune disease characterized by chronic inflammation of the synovial joints and progressive erosion of the articular cartilage matrix. Although the etiology and pathology of rheumatoid arthritis is not totally understood, certain parameters are always present. Cytokines, free radicals, reactive oxygen species and degrading enzymes are formed as a result of phagocytic activity in the rheumatoid arthritis affected joint. Inflammatory mediators such as IL1, TNF, MMPs, RNOs have long been implicated as mediators of articular damage in rheumatoid arthritis as well as low molecular weight HA. The biological response to the presence of these products in rheumatoid arthritis joints may explain the increase in GAG levels present as the body's defense mechanisms become overwhelmed as the disease progresses.

While not wishing to be bound by any particular theories of activity, it is postulated herein that the body's normal response to rheumatoid arthritis may not be effective in controlling its pathology, and an endogenous increase of specific GAGs, as provided by the compositions of the invention, will result in a more favorable long term response to treatment of rheumatoid arthritis. The invention provides the administration of a multiple GAG formulation as set forth herein will reduce the production and presence of the aforementioned inflammatory mediators via specific biological and chemical pathways.

Accordingly, the invention provides methods of treatment of rheumatoid arthritis comprising periodic administrations of therapeutic amounts of the compositions of the invention. It can be appreciated by one of skill in the art that the treatment regimen (e.g., frequency of administration and dosage) will vary according to the history, signalment, clinical stage and/or severity of the rheumatoid arthritis disease in a particular subject. In certain embodiments of the invention, the compositions of the invention may be used in conjunction with other known rheumatoid arthritis treatment agents such as, e.g., DMARDs, TNF blockers, IL-1Ras, immunosupressants and the like.

One preferred method provided by the invention is a first treatment regimen comprising a pretreatment with, e.g., a suitable DMARD, TNF blocker, or other immunosuppressant in conjunction with the composition of the invention, or as a separate pre-treatment to provide a systemic short term downregulation of the disease process, followed by a second regimen of treatment with the compositions of the invention to normalize and stabilize the body's response to alleviate the symptoms of rheumatoid arthritis on a long term basis without the deleterious side effects of e.g., systemic immunosuppressant agents such as TNF blockers. It is contemplated that the initial treatment regimen with, e.g., a suitable DMARD, TNF blocker or other immunosuppressant can be in conjunction with therapeutic amounts of the compositions of the invention.

In yet another embodiment of the invention the compositions set forth herein can further comprise a therapeutically effective amount of other suitable therapeutics including, but not limited to, antibiotics. For instance, suitable antibiotics for use in the compositions provided herein include, but are not limited to any of the antibiotics that can be adapted for intra-articular use, (see, e.g., "Infectious Arthritis" Alicia L. Bertone, pp. 397-409, in JOINT DISEASE IN THE HORSE", W. B. Sanders, 1996 (ISBN 0-7216-5135-6)). As can be appreciated by one of skill in the art, the choice of antibiotics and other suitable therapeutics, and their therapeutically effective amounts, can depend many factors including, but not limited to, e.g., the etiology of the infectious organism being treated or personal preference of the treating veterinarian or physician.

The compositions of the invention can also further comprise or exclude other therapeutic agents insofar as it is generally used as a therapeutic for connective tissue disease (e.g., tendonitis). Examples of other such therapeutic agents include, but are not limited to, synthetic and non-synthetic corticosteroid agents, nonsteroidal anti-inflammatory drugs, antirheumatics, immunoregulators, immunosuppressant, articular function augmenters, and interleukin production inhibitors. Specific examples of corticosteroid agents include, but are not limited to dexamethasone, hydrocortisone, triamcinolone, betamethasone, predonisolone, methylpredonisolone, halopredone, beclomethasone and the like.

Specific examples of non-steroidal anti-inflammatory agents include, but are not limited to diclofenac, indomethacin, ibuprofen, ketoprofen, aspirin, diflunisal, fulfenamic acid, floctafenine, tolfenamic acid, sulindac, fenbufen, salicylic acid, acemetacin, proglumetacin, nabumetone, protizinic acid, thiaprofen, oxaprozin, loxoprofen, alminoprofen, zaltoprofen, flurbiprofen, flurbiprofen and the like.

In one embodiment, the compositions of present invention can further comprise at least one pyrazolyl benzenesulfonamide compound, e.g., as set forth in U.S. Pat. No. 5,756,529 and U.S. Pat. No. 5,466,823, the contents of which are incorporated herein by reference. In particular, the compositions of the invention can further comprise a diaryl substituted pyrazole useful for treatment of inflammation and/or pain. It is specifically contemplated that the compositions of the invention can further comprise therapeutic amounts of any of the class of diaryl substituted pyrazoles their isomers, analogs and/or metabolites. In particular, these compounds reduce inflammation and/or pain primarily via inhibition of cyclooxygenase-2 (COX-2). In a preferred embodiment of the invention, the compositions provided further comprise a non-steroidal agent that reduces inflammation and/or pain primarily via inhibition of cyclooxygenase-2 (COX-2) and with the substantial absence of inhibition of cyclooxygenase-1 (COX-1). Examples of suitable diaryl substituted pyrazoles for use in the compositions of the invention, include, but are not limited to, celecoxib, rofecoxib and the like.

Examples of other agents which may be added to the core compositions set forth herein include, axetil, piroxicam, tenoxicam, ampiroxicam, meloxicam, D-penicillamine, bucillamine, gold sodium thiomalate, auranofin, lobenzarit, salazosulfapyridine, methotrexate, cyclophosphamide, azathioprine, mizoribine, cyclosporin and the like.

In a particularly preferred embodiment, the invention also provides a composition comprised of therapeutically effective amounts of chondroitin sulfate, N-acetyl D-glucosamine, hyaluronan, and a suitable antioxidant or free radical scavenger. In one embodiment, the compositions of the invention can further comprise a therapeutic amount of suitable superoxide dismutase (SOD) or other antioxidant including, but not limited to, examples set forth in U.S. Pat. No. 6,127,356 to Crapo et al., the contents of which are incorporated herein by reference.

The present invention further provides a method for treating connective tissue damage in humans or in animals comprising administering to a man or animal in need thereof, a therapeutically effective amount of a composition comprising chondroitin sulfate, N-acetyl D-glucosamine, and hyaluronan. In one preferred embodiment, the composition is directly applied to the affected connective tissues. In another preferred embodiment, the composition provided herein is adapted for intra-articular and/or systemic or parenteral administration. Systemic administrations can include, but are not limited to, intramuscular, intravenous or subcutaneous injection. The connective tissue damage referred herein include any primary or secondary diseases or injuries to the connective tissues in humans and/or animals. Such diseases or injuries include, but are not limited to, arthritic diseases, osteoarthritis (OA), rheumatoid arthritis (RA), osteochondrosis dessicans (OCD), cartilage damage, joint injuries, joint inflammation, joint synovitis, degenerative joint disease (DJD), post surgical DJD, traumatic injuries, fractures, tendon damage, ligament damage, skeletal damage, musculoskeletal damage, bone damage, fiber damage, adipose tissue damage, blood cell damage, and plasma damage.

One skilled in the art will understand that, in a method for treating diseases of connective tissue, therapeutic dosage will vary according to the specific condition being treated and the severity of the disease, etc., and, therefore, can be given in a single dose, and then repeated as needed, or the dosage can be given incrementally in several smaller dosages. Thus, the compositions of the present invention can be formulated such that the recommended therapeutic dose is achieved by the administration of a single dose or by the administration of several smaller doses. In certain methods, the injection is given systemically every 3-4 days to weeks, and the intralesional injection may be a single injection or a series of injections at, e.g., 3-week intervals.

It is apparent to one skilled in the art that the compositions of this invention can be included in a commercial package together with instructions for its use against a disease of connective tissue. Thus, the present invention further provides a kit comprising one or more containers comprising the composition provided herein, which comprises a therapeutically effective amount of chondroitin sulfate, N-acetyl D-glucosamine, and hyaluronan, and instructions for use the composition for treating connective tissue damages in man or in animals. The kit provided herein can also include other separate containers for other drugs, agents, compounds having desired therapeutic effects, including, but not limited to, synthetic and non-synthetic corticosteroid agents, nonsteroidal anti-inflammatory drugs, antirheumatics, immunoregulators, immunosuppressant, articular function augmenters, and interleukin production inhibitors.

The composition provided in the kit can be stored in any suitable container, including, but not limited to, syringes and vials, and in various dosage units. Preferably, the dosages for chondroitin sulfate and N-acetyl D-glucosamine are from between about 0.5 grams to about 1.5 grams per unit dose, respectively, and the dosage for hyaluronan is from about 10 mg to about 50 mg per unit dose. The chondroitin sulfate, N-acetyl D-glucosamine, and hyaluronan provided in the kit are formulated in sterile solutions, suspensions, or any pharmaceutically acceptable formulations, and stored in suitable containers, separately or in combination, in various dosage units. Preferably, the containers in the kit containing the compositions provided herein are disposable.

In one preferred embodiment, the kit contains multiple preloaded syringes. At least one syringe is preloaded with a preselected volume of from between about 2 and about 10 ml of the compositions of the present invention in a sterile solution comprised of proportionate weight to volume ratios of the composition comprised of e.g., about 1 gram of chondroitin sulfate as a mixture of about 40% CS4 and 60% CS6 chondroitin sulfate, about 1 gram of N-acetyl D-glucosamine, and about 20-40 mg but especially about 30 mg of hyaluronan (e.g., sodium hyaluronate) per unit dose of the composition. The preloaded syringe volume will of course vary depending upon the state of disease at the target tissue and species of animal, etc. The kit can also contain one or more separate syringes preloaded with a desired amount of other therapeutics well known in the art. In yet another preferred embodiment, the kit contains at least three separate containers, one contains chondroitin sulfate, such as CS4 or CS6, or a mixture of 40% CS4 and 60% CS6, one contains N-acetyl D-glucosamine, and one contains hyaluronan (e.g., sodium hyaluronate). The three components are mixed in a desired dosage unit before it is administered.

In yet another preferred embodiment, the kit provided herein contains a material adapted for implantation onto or between tissues of a mammalian body and with the composition attached thereon. Preferably, the material is in the form of malleable semi-solid substrate, or a mesh or gauze-like carrier, and is dissolvable or biodegradable. Preferably, the composition is impregnated into the material or coated onto the material or joined to the material by adhesion and/or capillary action, such as to a mesh, gauze, or gauze-like material. Alternatively, the composition is attached to the material that also includes, but is not limited to, a bandage, a surgical suture or staple material, and surgical device, such as buckle, suitable for a surgical process or device.

Furthermore, the kit provided herein includes instructions indicating a method of use of the composition for treating any primary or secondary diseases or injuries to the connective tissues in humans or animals. Such diseases or injuries include, but are not limited to, arthritic diseases, osteoarthritis (OA), rheumatoid arthritis (RA), osteochondrosis dessicans (OCD), cartilage damage, joint injuries, joint inflammation, joint synovitis, degenerative joint disease (DJD), post surgical DJD, traumatic injuries, fractures, tendon damage, ligament damage, skeletal damage, musculoskeletal damage, bone damage, fiber damage, adipose tissue damage, blood cell damage, and plasma damage. Instructions are normally in the form of a written material but are not limited to such.

Having discussed the composition of the present invention, and the method of use thereof, providing an enhanced effectiveness for the treatment of connective tissue damages, it will be more clearly perceived and better understood from the following specific examples which are intended to provide examples of certain preferred embodiments and not limit the present invention.

EXAMPLES

Example 1

A three-year old intact male thoroughbred racehorse, presented with an enlarged mid right front leg. The leg was sore upon palpation accompanied by heat underlying the affected area. The subject horse had been racing in graded stakes company with the injury being discovered two days post race. Diagnostic ultrasound of the affected area revealed a thirty percent (30%) grade III core lesion of the superficial digital flexor from zone 1B through zone 3A. A tendon splitting surgical procedure was performed using a 16 gauge needle directed into the core of the lesion from caudal to cranial at half inch intervals. At each of the six tendon splitting sites 0.5 ml a composition comprised of chondroitin sulfate, N-acetyl D-glucosamine, and hyaluronic acid (commercially available as POLYGLYCAN®, ArthroDynamic Technologies, Lexington, Ky.) was injected directly into the core lesion.

Post operative care included a two week hypertonic sweat of the affected leg accompanied by handwalking. At thirty days post surgery the subject horse was turned out into a small paddock for limited exercise. At sixty days post surgery and treatment with the composition of the invention, ultrasound examination revealed complete repair of the core lesion in zones 1B and 2A and a fifteen percent (15%) grade 1 lesion in zones 2B and 3A. At 150 days post surgery and treatment, the ultrasound of the superficial digital flexor tendon still revealed hyperechoic areas in zone 3A; however, overall good quality fiber structure was evident throughout the tendon including the zones previously containing the core lesion. At eight months post surgery and treatment, the tendon ultrasounded within normal limits, except that in zone 3A there was mild enlargement with a haphazard fiber pattern on caudal edge. The subject horse resumed training at eight months post treatment, and at ten months the tendon remained unchanged with horse in full racing training.

Example 2

A four-year old castrated male thoroughbred race horse presented with a chief complaint of an acute forelimb lameness of the left forelimb, grade 2 out of 5. History of the present illness included an acute lameness after galloping. Findings upon exam included increased degree of lameness upon flexion, and palpation of upper suspensory ligament increased lameness two fold for several steps. To confirm the diagnosis, the suspected suspensory ligament was blocked with 6 ml of carbocaine from the lateral edge and the horse jogged sound approximately five minutes later. Ultrasound examination of the upper suspensory ligament revealed a mild desmitis; however, no tearing of the ligamentous fibers was found.

Treatment: The following day, the origin of the suspensory was injected from the lateral edge with 2.5 ml of a composition comprised of chondroitin sulfate, N-acetyl D-glucosamine, and hyaluronic acid (commercially available as POLYGLYCAN®, ArthroDynamic Technologies, Lexington, Ky.) using a 21 gauge needle. The subject horse was walked for three days post injection and then resumed training. The horse remained sound at three weeks post injection wherein the horse won an allowance race and remained sound following a successful return to racing.

Example 3

A four-year old intact male thoroughbred racehorse presented with a chief complaint of an enlarged mid left front leg, sore upon palpation accompanied by heat. History of the present illness included the subject horse returning lame after a grade 2 stakes win. Findings by diagnostic ultrasound examination included a twenty-two percent (22%) grade II core lesion of the left front superficial digital flexor from zone 1B through 2B.

Treatment consisted of a tendon splitting surgical procedure of the affected area of the superficial digital flexor tendon using a 16 gauge needle directed into the core of the lesion from caudal to cranial at half inch intervals. At each of the five tendon splitting sites 0.5 ml of a composition comprising chondroitin sulfate, N-acetyl D-glucosamine, and hyaluronic acid (commercially available as POLYGLYCAN®, ArthroDynamic Technologies, Lexington, Ky.) was injected, using a 21 gauge needle such that a total of 2.5 ml of the composition of the invention was used. Post surgical and injection treatment consisted of a two week hypertonic sweat applied to the affected limb with the subject animal being limited to handwalking.

At thirty days post surgery the horse was turned out into a small paddock. At sixty days post surgery, follow-up ultrasound examination of the superficial digital flexor tendon revealed a ten percent (10%) grade 1 core lesion in zones 1B through 2B. At one hundred twenty days post surgery a follow-up ultrasound revealed complete resolution of the original core lesion. At two hundred forty days post surgery, the follow-up ultrasound examination revealed a normal structure to the tendon. The horse resumed training and has raced again at the allowance level finishing second place. The tendon remained within normal limits of palpation following a successful return to racing and no further ultrasounds examinations were conducted.

Example 4

An adult male domestic longhaired cat presented with a history of anorexia and intermittent vomiting and diarrhea of approximately three to four days duration. The subject animal had a previous history of temporary intestinal obstruction due to hairball formation in the small intestine. Physical examination revealed a thickened area of small intestine in the left cranial abdomen. Radiographs of the abdomen showed a thickened area of small intestine and radiographic findings consistent with neoplasia or a chronic partial obstruction. An exploratory celiotomy was performed and a diseased area of proximal small intestine approximately 10-12 inches in length was identified. The walls of the intestine were thickened and the functional lumen of the intestine was reduced at the affected area. Several areas of focal necrosis and mesenteric adhesions were present. Approximately 15 inches of small intestine were resected to remove the diseased portion and the two healthy ends of intestine were anastamosed.

Prior to closure of the abdomen, the area of the intestinal anastamosis was coated with approximately 4 ml of a composition comprised of chondroitin sulfate, N-acetyl D-glucosamine, and hyaluronic acid according to the invention. Closure of the abdomen was routine and the animal was placed on prophylactic antibiotics following surgery. Recovery from the surgery was uneventful and following a restricted diet and cage confinement, the animal returned to normal activity within about two weeks. Follow-up examination of the surgical sight revealed no significant findings, no post surgical abdominal adhesions were noted on physical examination and follow-up radiographs and ultrasound examination were without significant findings.

The foregoing description of preferred embodiments of the invention have been presented for purposes of illustration and description. They are not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilise the invention in various embodiments and with various modifications as are suited to the particular use contemplated. All such modifications and variations are within the scope of the invention as determined by the appended claims when interpreted in accordance with the breadth to which they are fairly, legally and equitably entitled.

We claim:

1. A method for treating connective tissue damage in a mammal comprising parenterally administering to a mammal in need thereof, a therapeutically effective amount of a composition comprising therapeutic amounts of chondroitin sulfate, N-acetyl D-glucosamine, and hyaluronan, wherein said connective tissue is selected from the group consisting of tendon, ligament, and bone.

2. The method of claim 1, wherein the therapeutically effective amount of chondroitin sulfate comprises from between about 0.5 grams to about 1.5 grams of a suitable chondroitin sulfate per unit dose of the composition.

3. The method of claim 2, wherein the suitable chondroitin sulfate is chondroitin 4-sulfate, chondroitin 6-sulfate, or a mixture thereof.

4. The method of claim 1, wherein the therapeutically effective amount of N-acetyl D-glucosamine is from about 0.5 grams to about 1.5 grams of N-acetyl D-glucosamine per unit dose of the composition.

5. The method of claim 1, wherein the therapeutically effective amount of hyaluronan is from about 10 mg to about 50 mg of hyaluronan per unit dose of said composition.

6. The method of claim 1, wherein the composition is a sterile solution for parenteral administration or dispersed onto or within a deformable semi-solid or solid material adapted for implantation onto or between tissues of a human or animal body.

7. The method of claim 6, wherein said material is dissolvable or biodegradable and in the form of a mesh, gauze, bandage, a surgical suture, or staple material suitable for a surgical process or device.

8. The method of claim 1, wherein the composition is administered in combination with one or more therapeutic agents.

9. The method of claim 8, wherein the therapeutic agent is selected from the group consisting of a synthetic or a non-synthetic corticosteroid agent, nonsteroidal anti-inflammatory agent, antirheumatic agent, immunoregulatory agent, immunosuppressant agent, articular function augmentory agent, and interleukin production inhibitor.

10. The method of claim 9, wherein said therapeutic agent is a corticosteroid agent.

11. The method of claim 9, wherein said therapeutic agent is a growth factor.

12. The method of claim 9, wherein said therapeutic agent is a tissue or a stem cell having a therapeutic effect.

13. A method for treating connective tissue damage in a mammal comprising parenterally administering to a mammal in need thereof, a therapeutically effective amount of a composition consisting essentially of therapeutic amounts of chondroitin sulfate, N-acetyl D-glucosamine, and hyaluronan, wherein said connective tissue is selected from the group consisting of tendon, ligament, and bone.

14. The method of claim 13, wherein the therapeutically effective amount of chondroitin sulfate comprises from between about 0.5 grams to about 1.5 grams of a suitable chondroitin sulfate per unit dose of the composition, and wherein the chondroitin sulfate is chondroitin 4-sulfate, chondroitin 6-sulfate, or a mixture thereof.

15. The method of claim 13, wherein the therapeutically effective amount of N-acetyl D-glucosamine is from about 0.5 grams to about 1.5 grams of N-acetyl D-glucosamine per unit dose of the composition.

16. The method of claim 13, wherein the therapeutically effective amount of hyaluronan is from about 10 mg to about 50 mg of hyaluronan per unit dose of said composition.

17. The method of claim 13, wherein the composition is a sterile solution for parenteral administration or dispersed onto or within a deformable semi-solid or solid material adapted for implantation onto or between tissues of a human or animal body.

18. The method of claim 17, wherein said material is dissolvable or biodegradable and in the form of a mesh, gauze, bandage, a surgical suture, or staple material suitable for a surgical process or device.

19. The method of claim 13, wherein the composition is administered in combination with one or more therapeutic agents.

20. The method of claim 19, wherein the therapeutic agent is selected from the group consisting of a synthetic or a non-synthetic corticosteroid agent, nonsteroidal anti-inflammatory agent, antirheumatic agent, immunoregulatory agent, immunosuppressant agent, articular function augmentory agent, and interleukin production inhibitor.

* * * * *